US012586486B2

(12) United States Patent
Park et al.

(10) Patent No.: US 12,586,486 B2
(45) Date of Patent: Mar. 24, 2026

(54) PROJECTED BLOODSTAIN GENERATOR AND METHOD OF GENERATING PROJECTED BLOODSTAIN USING THE SAME

(71) Applicant: REPUBLIC OF KOREA (NATIONAL FORENSIC SERVICE DIRECTOR MINISTRY OF THE INTERIOR AND SAFETY), Wonju-si (KR)

(72) Inventors: Nam Kyu Park, Bucheon-si (KR); Byung Seon Moon, Busan (KR); Jae Mo Goh, Seoul (KR); Jin Pyo Kim, Daejeon (KR); Young Il Seo, Wonju-si (KR); Eunah Joo, Wonju-si (KR); Jehyun Lee, Wonju-si (KR)

(73) Assignee: REPUBLIC OF KOREA (NATIONAL FORENSIC SERVICE DIRECTOR MINISTRY OF THE INTERIOR AND SAFETY), Wonju-si (KR)

( * ) Notice: Subject to any disclaimer, the term of this patent is extended or adjusted under 35 U.S.C. 154(b) by 944 days.

(21) Appl. No.: 17/848,575

(22) Filed: Jun. 24, 2022

(65) Prior Publication Data

US 2023/0326363 A1 Oct. 12, 2023

(30) Foreign Application Priority Data

Apr. 6, 2022 (KR) ........................ 10-2022-0042932

(51) Int. Cl.
*G09B 19/00* (2006.01)
*B05B 9/04* (2006.01)
*G01N 33/49* (2006.01)

(52) U.S. Cl.
CPC ............ *G09B 19/00* (2013.01); *B05B 9/0403* (2013.01); *G01N 33/49* (2013.01)

(58) Field of Classification Search
None
See application file for complete search history.

(56) References Cited

U.S. PATENT DOCUMENTS

2004/0227012 A1* 11/2004 Appleby ............. B05B 11/0059
239/334
2019/0385487 A1 12/2019 Park et al.

OTHER PUBLICATIONS

Office Action dated on Mar. 12, 2024, in connection with Korean Patent Application No. 10-2022-0042932, with English machine translation (9 pages).
Bandyopadhyay et al., "Analysis of Bloodstain Patterns at the Crime Scene due to Arterial Bleeding," International Journal of Development Research, Jan. 30, 2017, vol. 7, issue 1, pp. 10978-10983.

* cited by examiner

*Primary Examiner* — James B Hull
(74) *Attorney, Agent, or Firm* — Hauptman Ham, LLP

(57) ABSTRACT

A projected bloodstain generator includes: a blood supply capable of supplying blood by applying pressure; a blood vessel nozzle connector that is connected to the blood supply to transfer the blood and change a position for controlling the direction of blood ejection; and a blood vessel nozzle having one end connected to the blood vessel nozzle connector and the other end configured to eject blood by applied pressure.

8 Claims, 4 Drawing Sheets

PROJECTED BLOODSTAIN GENERATOR AND METHOD OF GENERATING PROJECTED BLOODSTAIN USING THE SAME

CROSS-REFERENCE TO RELATED APPLICATION

This application claims the benefit of Korean Patent Application No. 10-2022-0042932, filed on Apr. 6, 2022, in the Korean Intellectual Property Office, the disclosure of which is incorporated herein in its entirety by reference.

BACKGROUND

1. Field

One or more embodiments relate to a projected bloodstain generator and a method of generating a projected bloodstain using the same.

2. Description of the Related Art

In criminal cases, bloodstain pattern analysis plays an important role in reconstructing the scene of bloodshed.

Among bloodstain types, scattered bloodstains, which are formed by splashing blood, are important bloodstains that can be used to determine the act of hitting.

Among scattered bloodstains, a projected bloodstain is a bloodstain generated when blood spattered on a surface such as a wall when a victim's blood vessel is cut. The projected bloodstain is easy to morphologically confused with other scattered bloodstains (bloodstains formed when swinging a crime tool or bloodstains caused by actions such as hitting a bleeding area).

Therefore, it is important to establish objective criteria for determining a projected bloodstain. In order to establish objective criteria for determination in various surfaces and situations, a device for experimentally generating a projected bloodstain is needed.

SUMMARY

One or more embodiments include a projected bloodstain generator and a method of generating a projected bloodstain using the same. In more detail, one or more embodiments include a device and a method of experimentally generating a projected bloodstain formed by splashing blood on a surface such as a wall when a victim's blood vessel is cut at the scene of bloodshed.

One or more embodiments further include a device and a method of experimentally generating a projected bloodstain considering the size of blood vessels of the human body, the pressure of ejected blood, the direction of the blood ejection, and the like.

According to one or more embodiments, a projected bloodstain generator includes: a blood supply capable of supplying blood by applying pressure; a blood vessel nozzle connector that is connected to the blood supply to transfer the blood and change a position for controlling the direction of blood ejection; and a blood vessel nozzle having one end connected to the blood vessel nozzle connector and the other end configured to eject blood by applied pressure.

In an embodiment, the projected bloodstain generator may further include: a blood ejection device formed so that the blood vessel nozzle connector may move up and down or left and right in a state in which the blood vessel nozzle connector is mounted on the blood ejection device.

In an embodiment, the blood ejection device is formed in the shape of a dome on a plane located at a certain height from the ground, the blood vessel nozzle connector is mounted between a groove formed in the center, and the blood vessel nozzle connector may move up and down along the groove.

In an embodiment, the blood ejection device is formed to be rotatably movable on the plane located at a certain height from the ground, so that the blood vessel nozzle connector may move left and right.

In an embodiment, the projected bloodstain generator may further include: an input unit configured to receive an input signal according to operation information input by a user; and a control unit configured to control blood ejection according to the input signal received by the input unit.

In an embodiment, the operation information may include a magnitude of blood ejection pressure, a blood ejection angle, or an operation mode of the blood vessel nozzle during blood ejection.

According to one or more embodiments, a method of generating a projected bloodstain using a projected bloodstain generator includes: preparing blood in a blood supply of the projected bloodstain generator including the blood supply, a blood vessel nozzle connector, and a blood vessel nozzle; mounting a blood vessel nozzle prepared according to the purpose of an experiment on the blood vessel nozzle connector; and generating a projected bloodstain by applying pressure to the blood and operating the projected bloodstain generator.

In an embodiment, the projected bloodstain generator may further include an input unit and a control unit, and the generating of the projected bloodstain may include: inputting operation information into the input unit by a user; and generating a projected bloodstain by operating the projected bloodstain generator by the control unit according to the input operation information.

In an embodiment, the operation information may include a magnitude of blood ejection pressure, a blood ejection angle, or an operation mode of a blood vessel nozzle during blood ejection.

In an embodiment, the method of generating the projected bloodstain using the projected bloodstain generator may further include: analyzing the generated projected bloodstain.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
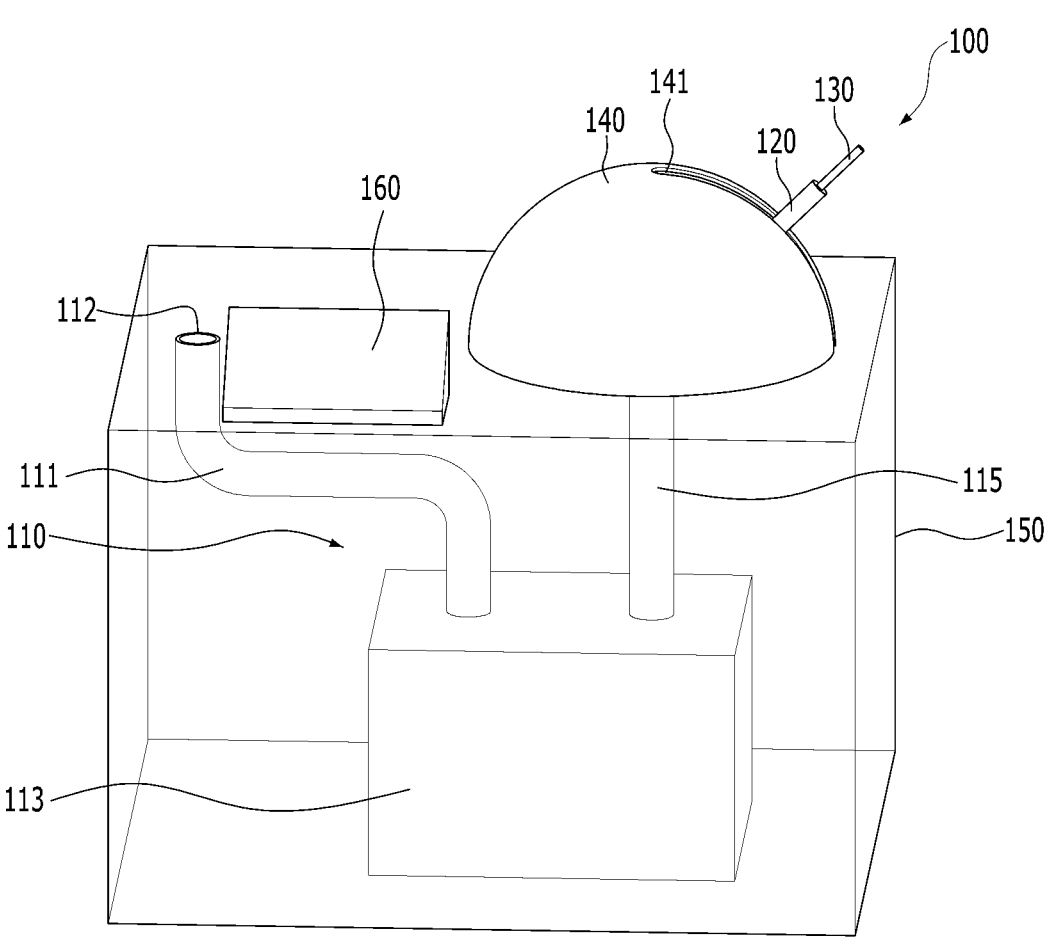
FIG. 1 is an exemplary view of a projected bloodstain generator according to an embodiment.

Hereinafter, embodiments will be described in detail with reference to the accompanying drawings. The same reference numerals are used to denote the same elements, and repeated descriptions thereof will be omitted.

It will be understood that although the terms "first," "second," etc. may be used herein to describe various components, these components should not be limited by these terms.

An expression used in the singular encompasses the expression of the plural, unless it has a clearly different meaning in the context.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly formed on the other layer, region, or component. That is, for example, intervening layers, regions, or components may be present.

Sizes of elements in the drawings may be exaggerated for convenience of explanation. In other words, since sizes and thicknesses of components in the drawings are arbitrarily illustrated for convenience of description, the following embodiments are not limited thereto. When a certain embodiment may be implemented differently, a specific process order may be performed differently from the described order. For example, two consecutively described processes may be performed substantially at the same time or performed in an order opposite to the described order.

It will be understood that when a layer, region, or component is connected to another portion, the layer, region, or component may be directly connected to the portion or an intervening layer, region, or component may exist, such that the layer, region, or component may be indirectly connected to the portion.

As used herein, the term 'projected bloodstain' refers to a bloodstain generated when blood that is ejected when a victim's blood vessel is cut is splashed on a surface, such as a wall.

Hereinafter, a projected bloodstain generator according to an embodiment will be described with reference to FIGS. 1 to 3.

Figure 2:
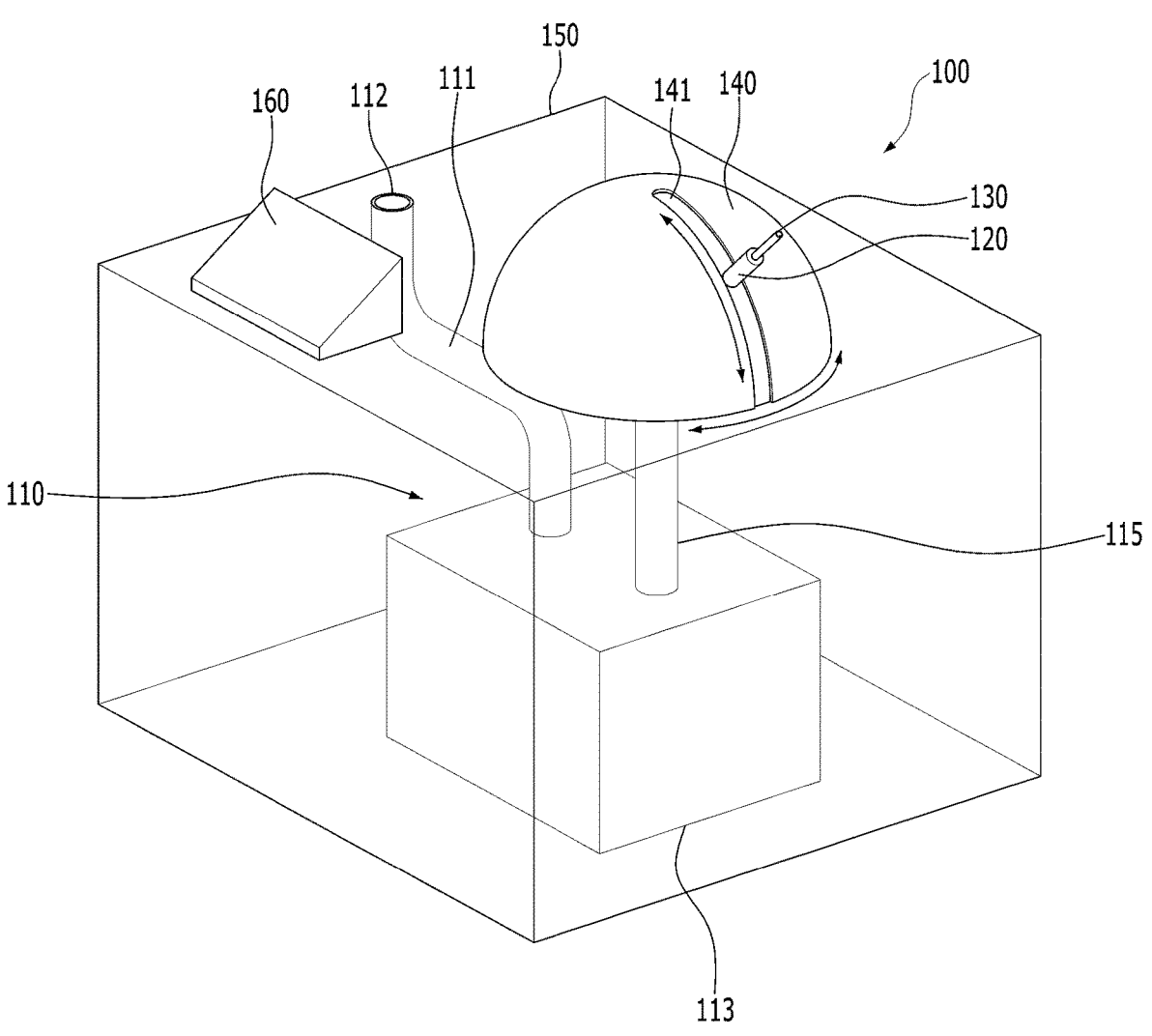
FIG. 2 is an exemplary view of a blood ejection device of a projected bloodstain generator according to an embodiment.

FIG. 1 is an exemplary view of a projected bloodstain generator according to an embodiment, and FIG. 2 is an exemplary view of a blood ejection device of a projected bloodstain generator according to an embodiment. FIG. 3 is a block diagram of a projected bloodstain generator according to an embodiment.

Figure 3:
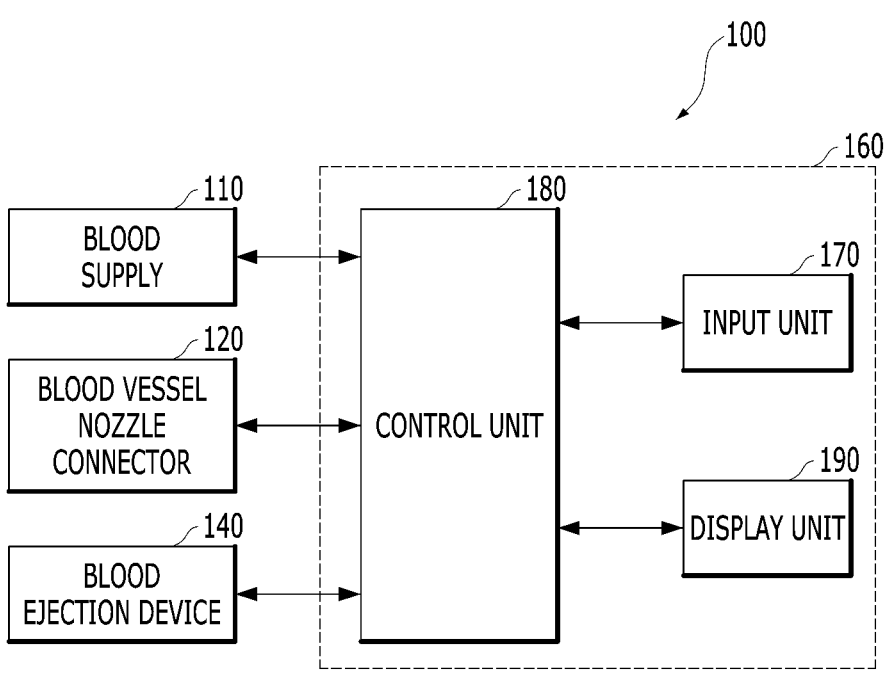
FIG. 3 is a block diagram of a projected bloodstain generator according to an embodiment.

Referring to FIGS. 1 to 3, a projected bloodstain generator 100 according to an embodiment may include a blood supply 110, a blood vessel nozzle connector 120, a blood vessel nozzle 130, a blood ejection device 140, an input unit 170, a control unit 180, and a display unit 190.

The blood supply 110 may supply blood by applying pressure. The blood supply 110 may be connected to the blood vessel nozzle connector 120 to be described later, and blood may be transferred through the blood vessel nozzle connector 120.

As an embodiment, the blood supply 110 of the projected bloodstain generator 100 may include a blood injection unit 111, a blood storage unit 113, and a blood transfer unit 115.

The blood injection unit 111 may have a blood inlet 112 formed at one end to inject blood or artificial blood. The blood injection unit 111 may be connected to the blood storage unit 113 by forming a path through which blood is transferred to the blood storage unit 113. In addition, the blood inlet 112 may be directly formed in the blood storage unit 113 without forming a separate blood injection unit 111.

The blood storage unit 113 is formed to store blood injected through the blood inlet 112. A pump (not shown) or the like may be installed inside the blood storage unit 113 to apply certain pressure to blood and discharge the blood to the outside of the blood storage unit 113.

The blood transfer unit 115 may be located on one side of the blood storage unit 113 to form a path through which blood is transferred by pressure. However, the blood transfer unit 115 may form a path through which blood is transferred inside the blood storage unit 113. As such, the shape and location of the blood transfer unit 115 is not limited to a specific shape and location. One end of the blood transfer unit 115 is connected to the blood storage unit 113, and the other end of the blood transfer unit 115 is connected to the blood vessel nozzle connector 120 to transfer blood from the blood storage unit 113 to the blood vessel nozzle connector 120.

The blood vessel nozzle connector 120 may be connected to the blood supply 110 to transfer blood, and is formed to be able to change a position for controlling the direction of blood ejection.

As an embodiment, the blood vessel nozzle connector 120 may be formed to be able to change the position for controlling the direction of blood ejection according to characteristics of the material. As another embodiment, the blood ejection device 140 to be described later may be used to change the position of the blood vessel nozzle connector 120.

One end of the blood vessel nozzle 130 may be connected to the blood vessel nozzle connector 120, and the other end of the blood vessel nozzle 130 may be formed such that blood is ejected by applied pressure.

An inner diameter of the blood vessel nozzle 130 may be formed in standards that match inner diameters of the wrist artery/vein, the elbow artery/vein, the carotid artery/vein, and the femoral artery/vein. The blood vessel nozzle 130 may be manufactured in various standards to correspond to various types of blood vessels in the human body according to the purpose of an experiment. A user may select one suitable for the purpose of the experiment from among various blood vessel nozzles 130, and connect one end of the selected blood vessel nozzle 130 to the blood vessel nozzle connector 120.

For example, by forming a thread on the outside of the blood vessel nozzle 130 and the inside of the blood vessel nozzle connector 120, the blood vessel nozzle 130 may be rotated and inserted into the blood vessel nozzle connector 120. As long as the blood vessel nozzle 130 may be rotatably mounted on the blood vessel nozzle connector 120, the connection method between the blood vessel nozzle 130 and the blood vessel nozzle connector 120 is not limited to a specific method.

The blood ejection device 140 may be formed so that the blood vessel nozzle connector 120 may move up and down or left and right in a state in which the blood vessel nozzle connector 120 is mounted on the blood ejection device 140.

As an embodiment, referring to FIGS. 1 and 2, the blood ejection device 140 may be formed in a dome shape on a plane located at a certain height from the ground. A groove 141 is formed vertically in the center of the dome-shaped blood ejection device 140, and the blood vessel nozzle connector 120 may be mounted between the groove 141. In this case, the blood vessel nozzle connector 120 may move up and down along the groove 141.

The dome-shaped blood ejection device 140 may rotate about an axis perpendicular to the plane on the plane located at a certain height from the ground. In this way, the blood ejection device 140 is rotated on the plane to enable left and right movement of the blood vessel nozzle connector 120.

As described above, the blood ejection device 140 enables the vertical and horizontal movement of the blood vessel nozzle connector 120, thereby controlling the direction of blood ejection ejected from the blood vessel nozzle 130 connected to the blood vessel nozzle connector 120.

However, the shape of the blood ejection device 140 is not limited to the above shape, and as long as the blood vessel nozzle connector 120 is movable up and down or left and right while the blood vessel nozzle connector 120 is mounted on the blood ejection device 140, the shape of the blood ejection device 140 is not limited to a specific shape.

The input unit 170 is a unit for receiving an input signal for controlling or operating the projected bloodstain generator 100 according to operation information input by a user, and may be implemented as various types of input units. For example, the input unit 170 may include a keyboard, a key pad, a touch pad, a jog wheel, a jog switch, and the like, but is not limited thereto.

In this case, the operation information may include a magnitude of blood ejection pressure, a blood ejection angle, or an operation mode of the blood vessel nozzle 130 at the time of blood ejection, in addition to information about a general operation of the projected bloodstain generator 100.

The magnitude of blood ejection pressure may be adjusted considering an actual bleeding site, the type of blood vessel, and the like that are to be reproduced through an experiment.

The blood ejection angle may be adjusted by changing the position of the blood vessel nozzle connector 120.

The operation mode of the blood vessel nozzle 130 may be set, for example, as follows. The blood vessel nozzle 130 may be rotated while being mounted on the blood vessel nozzle connector 120 to eject blood, or may be fixed in a non-rotating state so that blood is ejected. By adjusting the operation mode of the blood vessel nozzle, a user may select to eject blood in a rotating state of the blood vessel nozzle 130 or to eject blood in a non-rotating state of the blood vessel nozzle 130.

The control unit 180 may control all operations of the projected bloodstain generator 100. The control unit 180 may be implemented in various forms such as a central processing unit (CPU), a processor, a microprocessor, an application processor (AP), a micro controller unit (MCU), a microcomputer, or a mini computer. In addition, the control unit 180 may control the blood ejection according to an input signal received by the input unit 170.

The display unit 190 may display all operating states of the projected bloodstain generator 100. In addition, the display unit 190 may display operation information input by a user as described above.

The projected bloodstain generator 100 according to an embodiment may form the input unit 170, the control unit 180, and the display unit 190 into one control panel 160.

The control panel 160 may perform the function of the control unit 180 operating the projected bloodstain generator 100 according to an input signal received by the input unit 170 while performing the function of the input unit 170 receiving a user's touch input signal. In addition, the control panel 160 may also perform the function of the display unit 190 to display operation information input by a user, an operation state of the projected bloodstain generator 100, and the like.

The projected bloodstain generator 100 according to an embodiment may further include a housing 150.

The blood supply 110 may be accommodated in the housing 150, a plane may be formed on an upper portion of the housing 150 to place the dome-shaped blood ejection device 140, and the blood vessel nozzle connector 120 and the blood vessel nozzle 130 may be mounted on the blood ejection device 140. In addition, the control panel 160 may be formed on one side of the housing 150 to provide convenience to a user.

Figure 4:
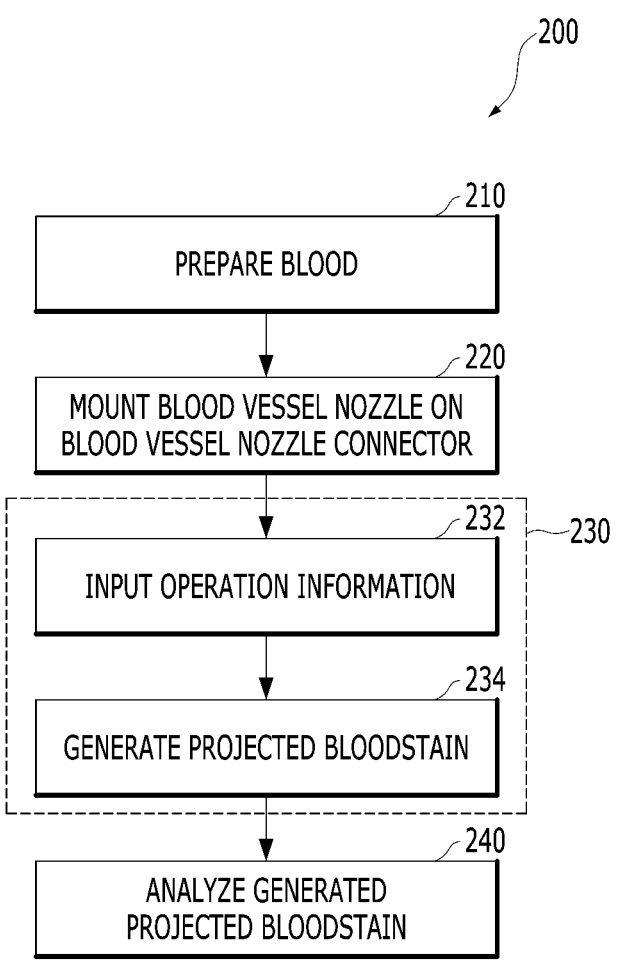
FIG. 4 is a flowchart illustrating a method of generating a projected bloodstain using a projected bloodstain generator according to an embodiment.

Hereinafter, a method 200 of generating a projected bloodstain using the projected bloodstain generator 100 according to an embodiment will be described with reference to FIG. 4. FIG. 4 is a flowchart illustrating the method 200 of generating a projected bloodstain using the projected bloodstain generator 100 according to an embodiment.

The projected bloodstain generator 100 according to an embodiment may further include the blood supply 110, the blood vessel nozzle connector 120, the blood vessel nozzle 130, the blood ejection device 140, the input unit 170, the control unit 180, and the display unit 190.

Operation 210 is preparing blood in the blood supply 110 of the projected bloodstain generator 100 according to an embodiment.

The blood supply 110 may include the blood injection unit 111, the blood storage unit 113, and the blood transfer unit 115. The blood supply 110 may inject blood or artificial blood through the blood injection unit 111, and may store blood. In this case, blood prepared for the experiment may include real human blood or artificial blood. In the case of artificial blood, it is preferable to prepare and use blood having physical properties similar to those of actual human blood.

Operation 220 is mounting the blood vessel nozzle 130 prepared according to the purpose of the experiment on the blood vessel nozzle connector 120. In this case, the blood vessel nozzle 130 may be manufactured in various standards to correspond to various types of blood vessels in the human body. A user may select the blood vessel nozzle 130 corresponding to the type of blood vessel suitable for the purpose of the experiment and may attach the blood vessel nozzle 130 to the blood vessel nozzle connector 120.

One end of the blood vessel nozzle 130 is connected to the blood vessel nozzle connector 120, and the other end is formed to eject blood. Blood may be received from the one end of the blood vessel nozzle 130 from the blood vessel nozzle connector 120 and ejected to the other end.

Operation 230 is generating a projected bloodstain by applying pressure to blood and operating the projected bloodstain generator 100.

In this case, operation 230 may include operations 232 and 234.

In operation 232, the user inputs operation information into the input unit 170. The operation information may include a magnitude of blood ejection pressure, a blood ejection angle, or an operation mode of the blood vessel nozzle 130 at the time of blood ejection, in addition to information about a general operation of the projected bloodstain generator 100.

Operation 234 may include generating a projected blood-stain by operating the projected bloodstain generator 100 by the control unit 180 according to the input operation information.

When the projected bloodstain generator 100 is operated, blood is ejected through the blood vessel nozzle 130 connected to the blood vessel nozzle connector 120 according to the operation information set by the user. As blood ejected around the projected bloodstain generator 100 is stained, a projected bloodstain is generated.

Operation 240 is analyzing the generated projected bloodstain.

Through the operation information input by the user and the analyzing of the shape of the generated projected bloodstain, the cause of the victim's bleeding at the scene of bloodshed may be revealed more clearly.

According to embodiments, the scene of bloodshed may be accurately reproduced considering the size of blood vessels of the human body, the pressure of ejected blood, the angle adjustment of a blood vessel when the blood is ejected, a rotational state of the blood vessel, and the like.

In addition, according to embodiments, because most of projected bloodstains generated at the scene of bloodshed may be reproduced, the scene of a violent crime such as a murder may be reproduced and analyzed more accurately and reliably.

It should be understood that embodiments described herein should be considered in a descriptive sense only and not for purposes of limitation. Descriptions of features or aspects within each embodiment should typically be considered as available for other similar features or aspects in other embodiments. Therefore, the scope of the disclosure is defined by the appended claims.

What is claimed is:

1. A projected bloodstain generator comprising:
a blood supply capable of supplying blood by applying pressure;
a blood vessel nozzle connector that is connected to the blood supply to transfer the blood and change a position for controlling a direction of blood ejection;
a blood vessel nozzle having one end connected to the blood vessel nozzle connector and the other end configured to eject blood by applied pressure, and
a blood ejection device formed such that the blood vessel nozzle connector moves up and down or left and right in a state in which the blood vessel nozzle connector is mounted on the blood ejection device, wherein the blood ejection device is formed in the shape of a dome on a plane located at a certain height from ground, the blood vessel nozzle connector is mounted between a groove formed in the center, and the blood vessel nozzle connector moves up and down along the groove.

2. The projected bloodstain generator of claim 1, wherein the blood ejection device is formed to be rotatably movable on the plane located at a certain height from the ground, so that the blood vessel nozzle connector moves left and right.

3. The projected bloodstain generator of claim 1, further comprising:
an input unit configured to receive an input signal according to operation information input by a user; and
a control unit configured to control blood ejection according to the input signal received by the input unit.

4. The projected bloodstain generator of claim 3, wherein the operation information comprises a magnitude of blood ejection pressure, a blood ejection angle, or an operation mode of the blood vessel nozzle during blood ejection.

5. A method of generating a projected bloodstain using a projected bloodstain generator, the method comprising:
preparing blood in a blood supply of the projected bloodstain generator including the blood supply, a blood vessel nozzle connector, and a blood vessel nozzle;
mounting a blood vessel nozzle prepared according to a purpose of an experiment on the blood vessel nozzle connector; and
generating a projected bloodstain by applying pressure to the blood and operating the projected bloodstain generator.

6. The method of claim 5, wherein the projected bloodstain generator further comprises an input unit and a control unit, and
the generating of the projected bloodstain comprises:
inputting operation information into the input unit by a user; and
generating a projected bloodstain by operating the projected bloodstain generator by the control unit according to the input operation information.

7. The method of claim 6, wherein the operation information comprises a magnitude of blood ejection pressure, a blood ejection angle, or an operation mode of a blood vessel nozzle during blood ejection.

8. The method of claim 5, further comprising:
analyzing the generated projected bloodstain.

* * * * *